US012788592B2

(12) United States Patent
Daudet

(10) Patent No.: US 12,788,592 B2
(45) Date of Patent: Nov. 10, 2026

(54) IMPLANT MADE MAINLY OF CERAMIC AND ASSEMBLY WITH GRIPPING AND POSITIONING DEVICE

(71) Applicant: FX SOLUTIONS, En-Bresse (FR)

(72) Inventor: Jean-Marie Daudet, En-Bresse (FR)

(73) Assignee: FX SHOULDER SOLUTIONS, Viriat (FR)

( * ) Notice: Subject to any disclaimer, the term of this patent is extended or adjusted under 35 U.S.C. 154(b) by 359 days.

(21) Appl. No.: 18/295,860

(22) Filed: Apr. 5, 2023

(65) Prior Publication Data

US 2023/0320869 A1 Oct. 12, 2023

(30) Foreign Application Priority Data

Apr. 8, 2022 (FR) ........................................ 2203270

(51) Int. Cl.

*A61F 2/40* (2006.01)
*A61F 2/32* (2006.01)
*A61F 2/38* (2006.01)
*A61F 2/46* (2006.01)

(52) U.S. Cl.

CPC .... *A61F 2/4612* (2013.01); *A61F 2002/4085* (2013.01); *A61F 2002/4627* (2013.01)

(58) Field of Classification Search

CPC ........ A61F 2/4612; A61F 2/4081; A61F 2/32; A61F 2/40; A61F 2/38; A61F 2/4014; A71F 2002/4085; A71F 2002/4627

USPC ................................ 623/19.11–19.13; 606/99

See application file for complete search history.

(56) References Cited

U.S. PATENT DOCUMENTS 5,951,564 A * 9/1999 Schroder ............... A61F 2/4607 606/100
6,027,505 A 2/2000 Rolf
2003/0055507 A1* 3/2003 McDevitt .............. A61F 2/4081 623/19.11
2003/0114933 A1* 6/2003 Bouttens ............... A61F 2/4081 623/19.13
2008/0077249 A1 3/2008 Gradel
2009/0270993 A1* 10/2009 Maisonneuve .... A61B 17/1778 623/19.14
2012/0253467 A1* 10/2012 Frankle ................. A61F 2/4081 623/19.11
2013/0150974 A1* 6/2013 Iannotti ................. A61F 2/4003 623/18.11
2013/0150975 A1 6/2013 Iannotti
2014/0194995 A1* 7/2014 Koka .................... A61F 2/4637 623/19.11
2020/0405491 A1* 12/2020 Cleveland ........... A61F 2/30749

FOREIGN PATENT DOCUMENTS

EP 2213261 8/2010
EP 3222250 9/2017

* cited by examiner

*Primary Examiner* — Jessica Weiss

(74) *Attorney, Agent, or Firm* — Defillo & Associates, Inc; Evelyn A. Defillo

(57) ABSTRACT

The invention relates to a joint prosthesis implant (1) made mainly of ceramic and having a housing (4) on its joint outer surface (8) and an assembly (100) of such an implant (1) and a gripping device (20).

9 Claims, 3 Drawing Sheets

IMPLANT MADE MAINLY OF CERAMIC AND ASSEMBLY WITH GRIPPING AND POSITIONING DEVICE

CROSS REFERENCE TO RELATED APPLICATION

This application claims priority French Patent Application No. FR2203270 filed Apr. 8, 2022.

FIELD OF THE INVENTION

The invention relates to a joint prosthesis implant. More specifically, the invention relates to a joint prosthesis implant whose joint outer surface is made of ceramic.

BACKGROUND OF THE INVENTION

The state of the art already describes several types of joint prosthesis, for example shoulder prostheses, hip prostheses, and knee prostheses.

These joint prostheses all comprise two implants, each having a joint outer surface intended to come into contact with each other, thus reproducing the joint. To reproduce the best possible joint quality, it is known to use pairs of favorable materials for these joint outer surfaces in contact, these pairs possibly consisting of two "hard" materials or one "hard" material and one "soft" material. The "hard" materials known and used in joint prosthesis implants are the cobalt-chromium alloy, titanium-stainless steel alloy and ceramic. The "soft" materials may be plastic, for example ultra-high-molecular-weight polyethylene (UHMWPE) and its cross-linked and vitamin-stabilized derivatives or polyetheretherketone (PEEK) or polyetherketoneketone (PEKK) and their derivatives.

The cobalt-chromium alloy is particularly appreciated by joint prosthesis implant manufacturers since it offers exceptional tribological and mechanical properties which allowed in particular the implant concerned to be impacted (using a suitable element) either directly into the patient's bone, or in an element itself attached to the patient's bone (for example a metaglene for a reverse total shoulder prosthesis), with no risk of damaging the implant.

However, the latest applicable standards (and in particular the updated standard of the delegated regulation (UE) 2020/217 of 4 Oct. 2019 REACH) tend to prohibit the use of chromium cobalt as material for the joint prosthesis implants since cobalt is considered to be a potentially carcinogenic, mutagenic or toxic substance for the patient. Alternative hard materials must therefore be considered.

One known hard material is ceramic. This material offers the advantage of being biocompatible and especially suitable for rubbing due to its hardness properties. However, ceramic is a material with very low ductility and the very high, localized mechanical stresses caused by the step of the surgeon gripping the implant could create cracks in the ceramic, or even break it. Such a risk is not acceptable, whether for the surgeon during the operation or for the patient who could need to have the prosthesis replaced too quickly. In addition, it is not currently authorized to install another ceramic implant when the ceramic of a first implant has broken. In this case therefore, another pair of materials must be chosen.

OBJECT AND SUMMARY OF THE INVENTION

The invention aims in particular to allow the use of such a ceramic implant which overcomes all the above-mentioned disadvantages.

The invention therefore relates to a joint prosthesis implant comprising:

- a main body made mainly of ceramic and comprising a joint outer surface made of ceramic, of concave or convex shape and
- a housing on the joint outer surface, the housing being configured to allow an assembly integral in rotation with a device for gripping the main body.

Thus, it is possible to produce a joint prosthesis implant made of ceramic (or mainly of ceramic) that is also functional, since it is particularly adapted to be assembled to a gripping device that is itself adapted to grip an implant in a fragile ceramic portion. Consequently, the risks of cracking or breaking are eliminated.

According to other optional characteristics of the implant taken alone or in combination:

- the housing comprises a hole crossing through the main body from one side to the other. This is a first embodiment of the invention;
- the housing comprises a blind hole located in the thickness of the main body. This is a second embodiment of the invention;
- the main body is a glenosphere;
- the diameter of the glenosphere is between 30 and 46 mm; and
- the main body is a ceramic tibial plateau, a knee condyle, an anatomic glenoid, a hip acetabulum or a ceramic cup.

The invention also relates to an assembly of a joint prosthesis implant according to the invention and a gripping device, the assembly comprising a guiding portion protruding from the main body of the implant, from a side of the main body opposite the joint outer surface.

According to other optional characteristics of the assembly taken alone or in combination:

- the gripping device comprises an assembly member intended to be installed in the housing and having a shape configured to allow an assembly integral in rotation with the main body of the implant;
- the protruding guiding portion is made in one piece with the main body; and
- the protruding guiding portion is one end of the assembly member.

The invention also relates to a joint prosthesis comprising an implant according to the invention.

The invention also relates to a use of an assembly according to the invention to form a joint prosthesis.

The invention also relates to a method for attaching an implant of the invention to form a joint prosthesis.

BRIEF DESCRIPTION OF THE FIGURES

The invention will be better understood on reading the following description, given solely by way of example and with reference to the accompanying drawings in which.

MORE DETAILED DESCRIPTION

Figure 1A:
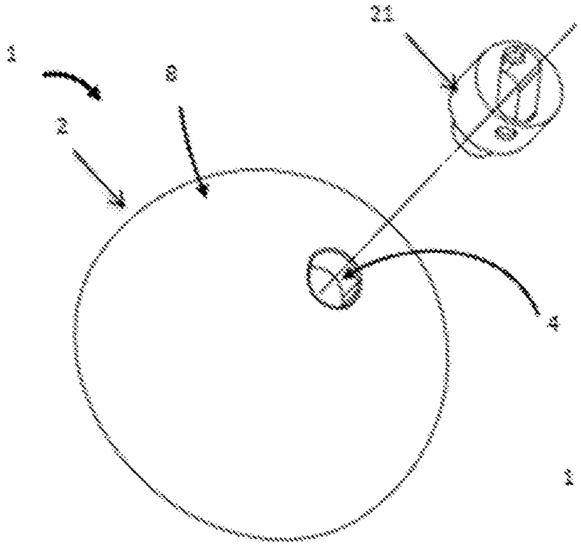
FIG. 1A shows a perspective front view of a first assembly according to the invention comprising an implant according to a first embodiment of the invention showing a housing provided on the joint outer surface having a blind hole.

FIGS. 1A to 3C show a joint prosthesis implant according to two different embodiments, designated by the general reference 1, and an assembly of such an implant and a gripping device, said assembly being designated by the general reference 100. The common elements are designated by the same references on these figures.

For the two embodiments shown, as well as for those not shown, the joint prosthesis implant 1 comprises:

- a main body 2 made mainly of ceramic and comprising a joint outer surface 8 made of ceramic, of concave or convex shape and
- a housing 4 on the joint outer surface 8, the housing 4 being configured to allow an assembly integral in rotation with a device 20 for gripping the main body 2.

In addition, and for all the embodiments shown, as well as for those not shown, the assembly 100 according to the invention comprises a joint prosthesis implant 1 according to one of the possible variants of the invention and a gripping device 20. Furthermore, the assembly 100 comprises a guiding portion 12 protruding from the main body 2 of the implant 1, from a side of the main body 2 opposite the joint outer surface 8.

Note that the various examples shown of the invention concern a glenoid implant 1 for reverse shoulder prosthesis but that the invention applies to any prosthesis comprising a joint implant having a ceramic joint surface and being assembled by the surgeon, on the patient's bone or on an intermediate element attached to said bone, by using a gripping device. It could be a hip prosthesis or a knee prosthesis (obviously, with an adaptation of the shape of the various elements forming this prosthesis). Thus, in all these examples, the main body 2 corresponds to a glenosphere 2.

Any type of ceramic known by those skilled in the art can be used for the main body. For example, it could be alumina, zirconia or a composite material. Since ceramic is a hard material, it can be used with pairs of "hard/hard" or "hard/soft" materials. In this second example, the "soft" material can be ultra-high-molecular-weight polyethylene (UHMWPE) or polyetheretherketone (PEEK) or polyetherketoneketone (PEKK) or their derivatives.

In the two embodiments of the implant 1, the main body 2 therefore corresponds to a glenosphere 2 intended to be impacted inside a metaglene 3, itself attached beforehand in the bone of the patient (not shown) who will receive surgery.

The glenosphere 2 and the metaglene 3 are assembled together by any means known by those skilled in the art, for example using a Morse cone (not shown) between the glenosphere 2 and the metaglene 3.

The ceramic glenosphere 2 can have a diameter from 30 to 46 mm, it can be centered or off-centered and can be lateralized with respect to the metaglene, if necessary.

In all the embodiments shown, the housing 4 and the part of the assembly member 21 intended to be installed in said housing 4 have an oblong shape. Thus, such an association of complementary oblong shape allows an assembly integral in rotation between the glenosphere 2 and the gripping device 20. Note that any other association of complementary geometric shape known by those skilled in the art and allowing such an assembly integral in rotation can be considered in the framework of the invention. The surgeon therefore has a safe gripping means presenting no risk of cracking or breaking the ceramic of the glenosphere 2 during surgery. This non-pivoting link between the glenosphere 2 and the assembly member 21 allows the surgeon to index the position of the glenosphere 2, during surgery, using the gripping device 20. Such a possibility of positioning the glenosphere 2 is particularly advantageous if the glenosphere is off-centered with respect to the metaglene 3, which may happen when the bone of the patient who will receive surgery does not allow the metaglene to be attached in the most natural position possible for the joint.

In addition, the housing 4 provided on the joint outer surface 8 comprises either a blind hole (FIGS. 1A to 2C), or a through-hole (FIGS. 3A to 3C) depending on the element carrying the guiding portion 12, as described below.

Figure 1B:
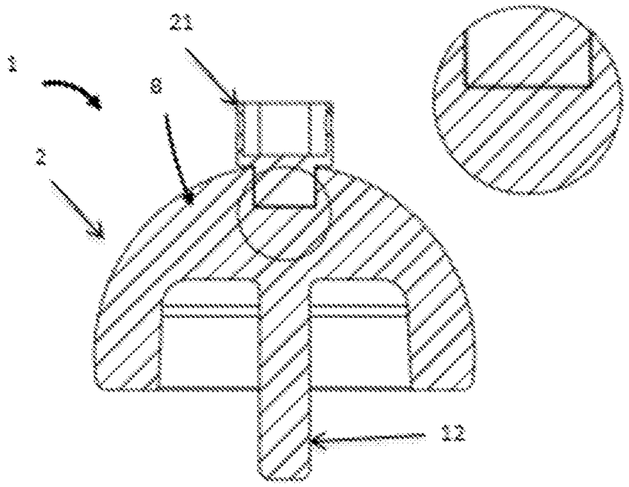
FIG. 1B shows a cross sectional view taken alone the line of FIG. 1A.
Figure 1C:
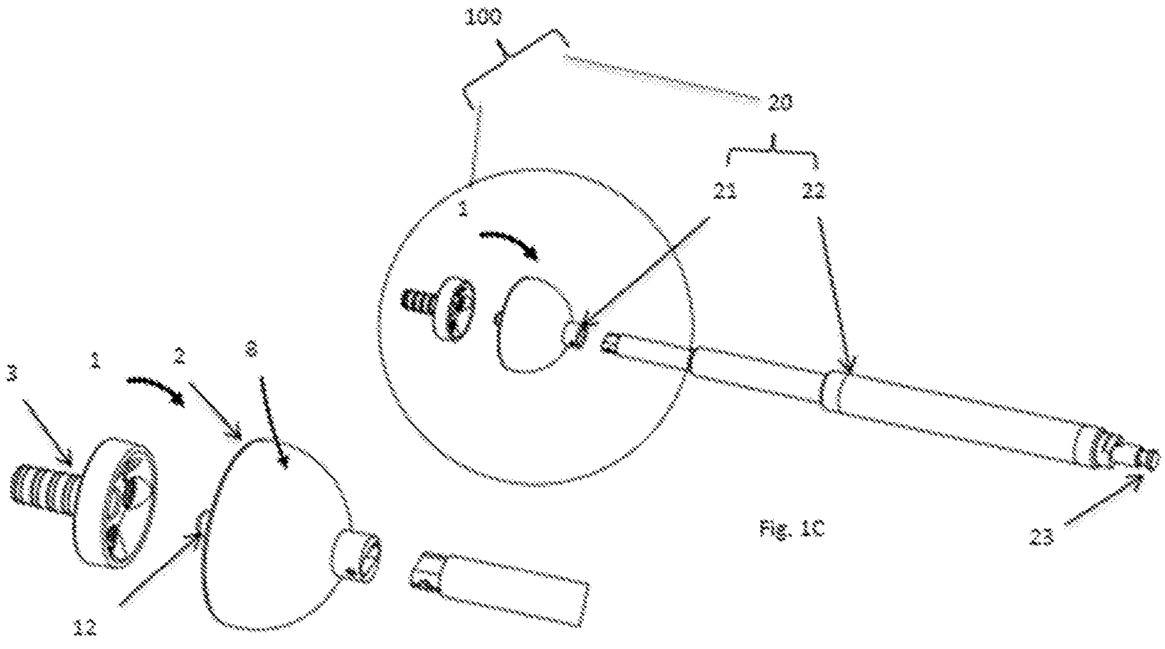
FIG. 1C shows a perspective front view of the first assembly of FIG. 1A showing the glenosphere and the metaglene.

The guiding portion 12 protruding from the glenosphere 2, from one side of the glenosphere 2 opposite its joint outer surface 8, guides the glenosphere using the gripping device 20 into the correct final position ready to be impacted inside the metaglene 3. According to the first embodiment of the implant 1 (referring to FIGS. 1A to 2C), this guiding portion 12 is made in one piece with the glenosphere 2 (FIGS. 1B and 2B). It is advantageously made in one piece when molding the glenosphere 2. Alternatively (FIGS. 3A to 3C), the protruding guiding portion 12 corresponds to a free end of the assembly member 21.

The gripping device 20, forming part of the assembly 100 of the invention, comprises the assembly member 21 and a main portion 22. More precisely, the assembly member 21 is located at one of the two ends of the main portion 22. In the examples shown on FIGS. 1A to 1C and 3A to 3C, the assembly member 21 and the main portion 22 are two separate elements, assembled together by clipping. Thus, it is possible to first position only the assembly member 21, which is advantageous since this makes it easier for the surgeon to assemble the assembly member 21 and the glenosphere 2, in particular when the guiding portion 12 is carried by said assembly member 21. Still according to these examples, the main portion 22 is provided, at its end opposite to that intended to be coupled to the assembly member 21, with a press stud 23 allowing the surgeon to unclip the main portion 22 and the assembly member 21, when the glenosphere 2 is correctly positioned inside the metaglene 3. The possibility of uncoupling the main portion 22 and the assembly member 21 offers another advantage for the surgeon for the remainder of the surgery. When the glenosphere 2 is positioned by the surgeon in the position required for the impaction step, the surgeon can in fact uncouple the assembly member 21 by pressing the press stud 23. Thus, the assembly member 21 remains in the housing 4 and can act as "buffer" member for the subsequent step of impacting the glenosphere 2 inside the metaglene 3. In other words, the surgeon can impact the glenosphere 2, to form the final prosthesis, via the assembly member with no risk of cracking or breaking the ceramic of the glenosphere 2.

Figure 2A:
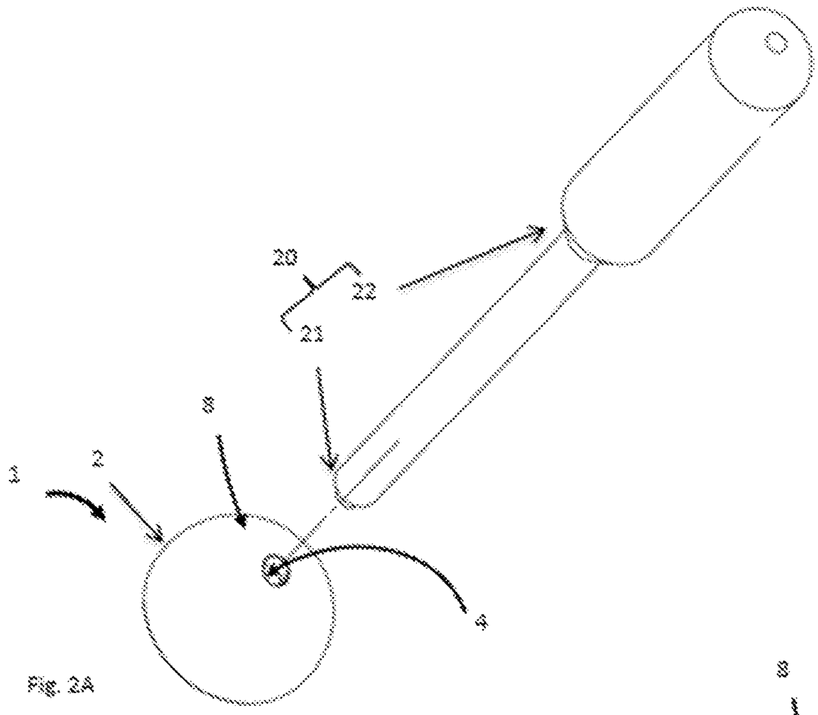
FIG. 2A shows a perspective front view of a second assembly according to the invention comprising the implant according to the first embodiment of the invention.
Figure 2B:
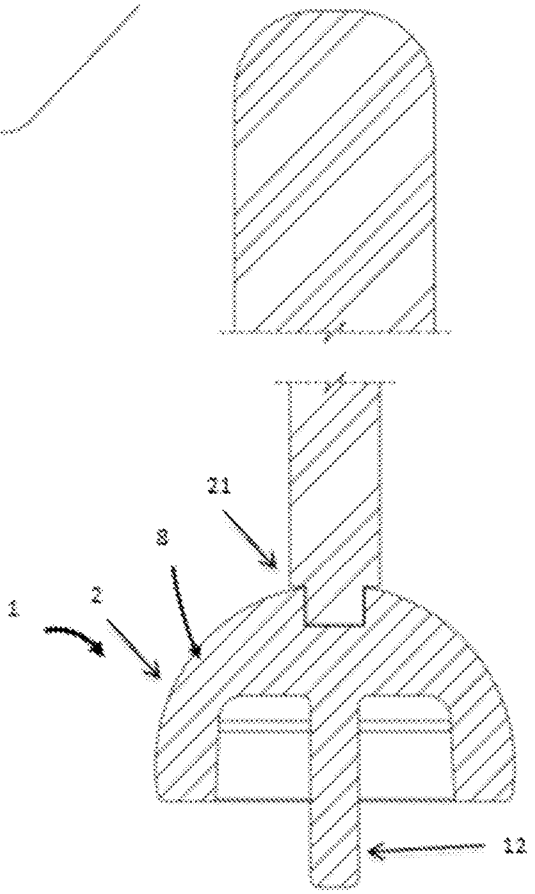
FIG. 2B shows a cross sectional view taken alone the line of FIG. 2A.
Figure 2C:
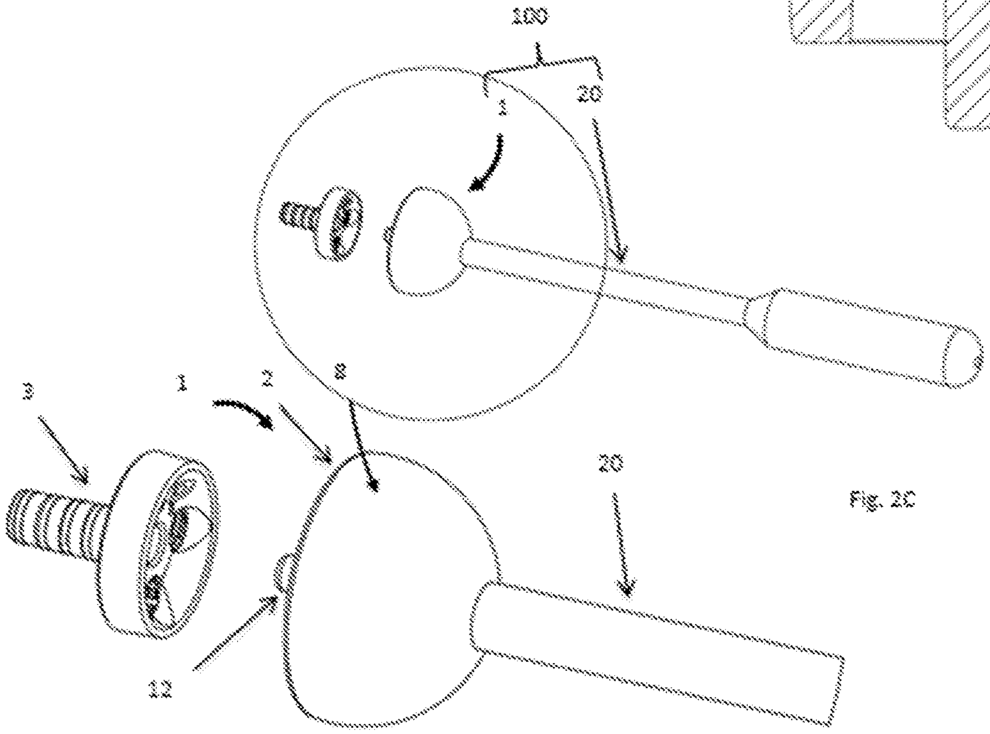
FIG. 2C shows a perspective front view of the first assembly of FIG. 2A showing the glenosphere and the metaglene.
Figure 3A:
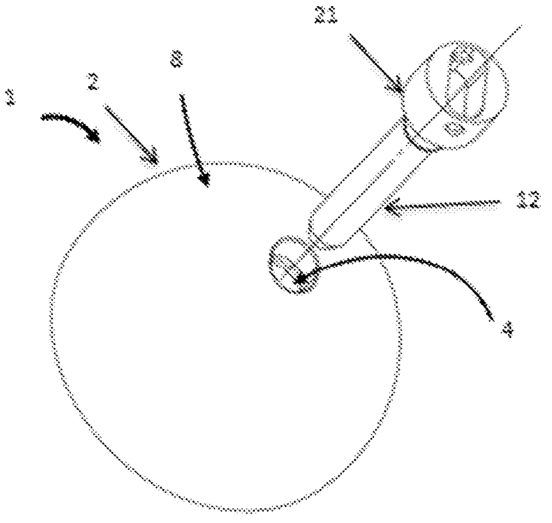
FIG. 3A shows a perspective front view of a third assembly according to the invention comprising an implant according to a second embodiment of the invention.
Figure 3B:
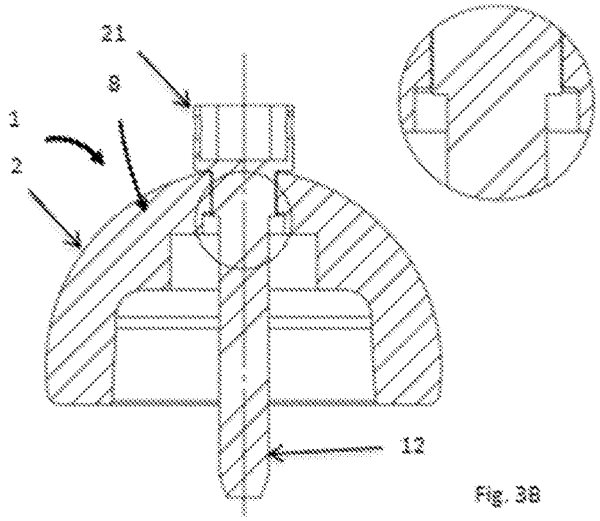
FIG. 3B shows a cross sectional view taken alone the line of FIG. 3A.
Figure 3C:
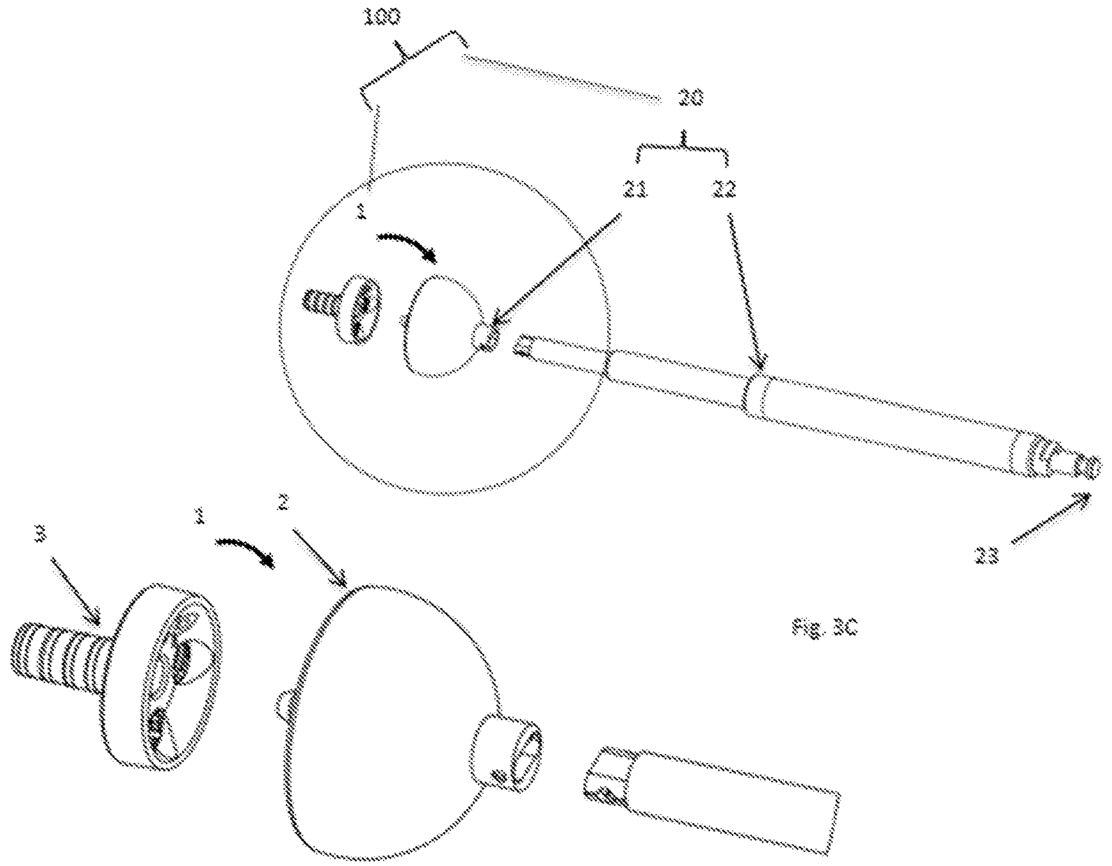
FIG. 3C shows a perspective front view of the first assembly of FIG. 3A showing the glenosphere and the metaglene.

Alternatively, and as shown on FIGS. 2A to 2C, the gripping device 20 is in one piece. In other words, the assembly member 21 is one end of said gripping device 20 and made in one piece with the rest of the latter. This alternative is advantageous since it means that the assembly member 21 does not have to be assembled separately, then clipped with a main portion 22 of the gripping device 20, which reduces the number of steps and handling operations for the surgeon. However, for the subsequent step of impacting the glenosphere inside the metaglene, the surgeon will not benefit from the presence of a buffer member and will therefore either have to impact the glenosphere 2 with a device designed especially for ceramic or position a buffer member.

The invention is not limited to the embodiments described. As mentioned previously, the invention can be applied to any type of joint implant having a ceramic joint surface and being assembled by the surgeon, on the patient's bone or on an intermediate element attached to said bone, by using a gripping device.

LIST OF REFERENCES

1: joint prosthesis implant
2: main body/glenosphere
3: metaglene
4: housing
8: joint outer surface
12: guiding portion
20: gripping device
21: assembly member
22: main portion of the gripping device
23: press stud
100: assembly of an implant and a gripping device

What is claimed is:

1. A joint prosthesis implant comprising:

a main body made mainly of ceramic and comprising a joint outer surface made of ceramic, and comprising a concave or convex shape, and a housing on the joint outer surface, the housing having a shape that is complementary to a shape of an assembly member to be installed in the housing, wherein the assembly member is adapted to be connected to a gripping device, wherein the complementary shapes of the housing and the assembly member allows the main body and the gripping device to rotate together, and wherein the housing has an oblong shape.

2. The joint prosthesis implant according to claim 1, wherein the housing comprises a hole extending through the main body from one side to the other.

3. The joint prosthesis implant according to claim 1, wherein the housing comprises a blind hole located within a thickness of the main body.

4. The joint prosthesis implant according to claim 1, wherein the main body is a glenosphere.

5. The joint prosthesis implant according to claim 4, wherein a diameter of the glenosphere is between 30 mm and 46 mm.

6. The joint prosthesis implant according to claim 1, wherein the main body is a ceramic tibial plateau, a knee condyle component, a glenoid component, a hip acetabulum component, or a ceramic cup.

7. An assembly comprising:

a joint prosthesis implant including: a main body made mainly of ceramic and comprising a joint outer surface made of ceramic, and comprising a concave or convex shape, and a housing on the joint outer surface, the housing having a shape that is complementary to a shape of an assembly member to be installed in the housing, wherein the assembly member is adapted to be connected to a gripping device, wherein the complementary shapes of the housing and the assembly member allows the main body and the gripping device to rotate together; and a guiding portion protruding from the main body of the implant from a side of the main body opposite the joint outer surface, and wherein the housing of the implant and a corresponding portion of the assembly member installed therein have complementary oblong shapes.

8. The assembly according to claim 7, wherein the guiding portion is made in one piece with the main body.

9. The assembly according to claim 7, wherein the guiding portion is one end of the assembly member.

* * * * *